(12) United States Patent
Bral (10) Patent No.: US 10,973,994 B2
(45) Date of Patent: Apr. 13, 2021

(54) MEANS AND METHOD TO INVADE SKIN, MUCOSA, AND UNDERLYING TISSUES WITH LITTLE OR NO PAIN

(71) Applicant: Pourang Bral, Passaic, NJ (US)

(72) Inventor: Pourang Bral, Passaic, NJ (US)

(*) Notice: Subject to any disclaimer, the term of this patent is extended or adjusted under 35 U.S.C. 154(b) by 202 days.

(21) Appl. No.: 14/028,500

(22) Filed: Sep. 16, 2013

(65) Prior Publication Data

US 2017/0095622 A1    Apr. 6, 2017

(51) Int. Cl.
| | | |
|---|---|---|
| A61M 5/00 | (2006.01) | |
| A61M 5/42 | (2006.01) | |
| A61N 1/04 | (2006.01) | |
| A61M 5/32 | (2006.01) | |
| A61B 5/151 | (2006.01) | |
| A61B 5/15 | (2006.01) | |
| A61N 1/36 | (2006.01) | |

(52) U.S. Cl.
CPC ......... *A61M 5/422* (2013.01); *A61B 5/15016* (2013.01); *A61B 5/150022* (2013.01); *A61B 5/150091* (2013.01); *A61B 5/15105* (2013.01); *A61B 5/150129* (2013.01); *A61B 5/150137* (2013.01); *A61M 5/3202* (2013.01); *A61M 5/3287* (2013.01); *A61N 1/0456* (2013.01); *A61N 1/36021* (2013.01); *A61B 5/15142* (2013.01); *A61B 5/150412* (2013.01); *A61B 5/150503* (2013.01); *A61M 2005/3267* (2013.01); *A61M 2205/0205* (2013.01); *A61M 2205/054* (2013.01); *A61M 2205/362* (2013.01); *A61M 2205/3606* (2013.01); *A61M 2205/582* (2013.01)

(58) Field of Classification Search
CPC .... A61M 2205/054; A61M 2205/3606; A61M 2205/362; A61M 5/422
See application file for complete search history.

(56) References Cited

U.S. PATENT DOCUMENTS

| | | |
|---|---|---|
| 1,561,116 A | 11/1925 | Silliman |
| 2,258,857 A | 11/1941 | McCann |
| 2,945,495 A | 7/1960 | Fosdal |
| 3,207,159 A | 9/1965 | Tateigi |
| 3,308,823 A | 3/1967 | Peterson |
| 3,467,104 A | 9/1969 | Burbridge |
| 3,620,209 A | 11/1971 | Kravitz |
| 3,820,209 A | 11/1971 | Kravitz |
| 3,626,929 A | 12/1971 | Sanz et al. |

(Continued)

OTHER PUBLICATIONS http://www.ncbi.nlm.nlh.gov/pmc/articles/PMC3001531/pdf/182e843-pdf Dec. 14, 2016, Reducing the Pain of Childhood Vaccination: on evidance-based clinical Practice guideline.

(Continued)

*Primary Examiner* — William R Carpenter (57) ABSTRACT

A means and a method is disclosed to diminish or eliminate the pain associated with a sharp object penetrating the skin, during such procedures as an injection, biopsy, or deriving a blood sample. To this end, repeated tapping, pressing, or rubbing or vibrating is performed over the skin at or near the site of penetration of the sharp object in conjunction with applying electricity on the skin. The invention discloses a method of using a skin-puncturing means, with enhanced features, to provide local anesthesia at the site of penetration of a sharp object.

19 Claims, 4 Drawing Sheets

(56) References Cited

U.S. PATENT DOCUMENTS

| | | | |
|---|---|---|---|
| 3,971,229 A | 7/1976 | Privas | |
| 4,046,142 A | 9/1977 | Whitney | |
| 4,243,035 A * | 1/1981 | Barrett | A61F 13/38 604/1 |
| 4,309,989 A | 1/1982 | Fahim | |
| 4,440,167 A | 4/1984 | Takehisa | |
| 4,676,257 A | 6/1987 | Halpern | |
| 4,701,167 A * | 10/1987 | Chekan | B65D 83/30 604/301 |
| 4,710,172 A | 12/1987 | Jacklich et al. | |
| 4,725,265 A * | 2/1988 | Sairenji | A61M 5/422 604/112 |
| 4,900,721 A * | 2/1990 | Bansemir | A01N 59/00 424/49 |
| 4,924,880 A | 5/1990 | O'Neill | |
| 5,035,704 A | 7/1991 | Lambert | |
| 5,088,925 A | 2/1992 | Mason | |
| 5,171,225 A | 12/1992 | Sterrett | |
| 5,271,622 A | 12/1993 | Kn | |
| 5,431,655 A | 7/1995 | Melker | |
| 5,437,606 A | 8/1995 | Tsukamoto | |
| 5,496,363 A | 3/1996 | Burgio | |
| 5,578,014 A * | 11/1996 | Erez | A61F 7/10 604/192 |
| 5,647,851 A | 7/1997 | Pokras | |
| 5,680,872 A | 10/1997 | Sesekura et al. | |
| 5,728,050 A | 3/1998 | Lin | |
| 5,730,753 A | 3/1998 | Morita | |
| 5,839,895 A | 11/1998 | Fishburne | |
| 5,857,983 A | 1/1999 | Douglas et al. | |
| 5,873,844 A | 2/1999 | Campero | |
| 5,873,887 A | 2/1999 | King et al. | |
| 5,891,053 A | 4/1999 | Sesekura | |
| 5,899,880 A * | 5/1999 | Bellhouse | A61M 5/3015 222/389 |
| 5,927,976 A | 7/1999 | Wu | |
| 5,954,738 A | 9/1999 | LeVaughn et al. | |
| 5,964,718 A | 10/1999 | Duchon et al. | |
| 6,045,567 A | 4/2000 | Taylor et al. | |
| 6,063,039 A | 5/2000 | Cunningham et al. | |
| 6,066,103 A | 5/2000 | Duchon et al. | |
| 6,099,503 A | 8/2000 | Stradella | |
| 6,135,769 A | 10/2000 | Kwan | |
| 6,155,992 A | 12/2000 | Henning et al. | |
| 6,200,308 B1 * | 3/2001 | Pope | A61B 18/203 606/11 |
| 6,217,561 B1 | 4/2001 | Gibbs | |
| 6,231,531 B1 | 5/2001 | Lum | |
| 6,419,490 B1 | 7/2002 | Weathers | |
| 6,454,743 B1 | 9/2002 | Weber | |
| 6,547,561 B2 | 4/2003 | Meller | |
| 6,599,272 B1 | 7/2003 | Hjertman | |
| 6,602,229 B2 | 8/2003 | Coss | |
| 6,626,887 B1 | 9/2003 | Wu | |
| 6,660,029 B2 | 12/2003 | VanSkiver et al. | |
| 6,706,000 B2 | 3/2004 | Perez et al. | |
| 6,708,060 B1 | 3/2004 | Avrahami | |
| 6,902,554 B2 | 6/2005 | Huttner | |
| 7,386,349 B2 | 6/2008 | Davar | |
| 7,503,927 B1 | 3/2009 | Vetanze | |
| 7,803,128 B2 | 9/2010 | Christensen | |
| 8,500,678 B1 * | 8/2013 | Leibovici | A61M 5/19 604/69 |
| 8,998,842 B2 * | 4/2015 | Lauchard | A61M 5/20 604/131 |
| 2001/0049510 A1 | 12/2001 | Burr | |
| 2001/0049540 A1 | 12/2001 | Burr | |
| 2002/0082522 A1 | 6/2002 | Douglas | |
| 2002/0128600 A1 | 9/2002 | Nissels | |
| 2002/0147446 A1 | 10/2002 | Eln-Gal | |
| 2002/0188223 A1 | 12/2002 | Perez et al. | |
| 2002/0193861 A1 | 12/2002 | Harrison | |
| 2003/0036034 A1 | 2/2003 | Kay | |
| 2003/0078534 A1 | 4/2003 | Hochman | |
| 2003/0100888 A1 | 5/2003 | Spinello | |
| 2004/0015188 A1 * | 1/2004 | Coulter | A61N 1/36021 607/3 |
| 2004/0092843 A1 | 5/2004 | Kreiser et al. | |
| 2004/0230227 A1 | 11/2004 | Avrahami | |
| 2005/0149145 A1 | 7/2005 | Coulter | |
| 2005/0177071 A1 | 8/2005 | Nakayama | |
| 2005/0177201 A1 | 8/2005 | Freeman | |
| 2006/0030824 A1 * | 2/2006 | Hunn | A61L 31/14 604/264 |
| 2006/0106363 A1 | 5/2006 | Aravena | |
| 2006/0173386 A1 | 8/2006 | Lindquist | |
| 2006/0217636 A1 | 9/2006 | Braig | |
| 2007/0088385 A1 | 4/2007 | Perry | |
| 2007/0106342 A1 | 5/2007 | Schumann | |
| 2007/0197968 A1 | 8/2007 | Pongpairochana | |
| 2007/0282400 A1 | 12/2007 | Gorham | |
| 2008/0039829 A1 | 2/2008 | Goldman | |
| 2008/0109049 A1 | 5/2008 | Schumann | |
| 2008/0125842 A1 | 5/2008 | Petitt | |
| 2008/0188779 A1 * | 8/2008 | Vallero | A61M 5/422 601/21 |
| 2009/0004628 A1 * | 1/2009 | Knutson | A61C 19/08 433/215 |
| 2009/0118789 A1 | 5/2009 | Buhlmann | |
| 2010/0030299 A1 | 2/2010 | Covalin | |
| 2010/0106088 A1 * | 4/2010 | Yodfat | A61M 5/158 604/112 |
| 2011/0022115 A1 | 1/2011 | Salzhauer | |
| 2011/0112477 A1 | 5/2011 | Bral | |

OTHER PUBLICATIONS

Author's Anna Taddio, Mary Appleton, Robert Borlulussi, Christine Chambers, Vnita Dubey, Scott Hulperin, Anita Hanrahan, Mosha Sop, Donna Lockett, Nomi MacDonald, Deans Mŕdmer, Michael Rirder, Jeffrey Scott, Vibhuti Shah. Publication: CMAS, Vol. 182(18) p. E847.
https://en.wikipedia.org/wiki/Refractory_Period_(physiology).
U.S. Appl. No. 13/134,013, Bral.
U.S. Appl. No. 12/927,136, Bral.
U.S. Appl. No. 13/550,826, Bral.
U.S. Appl. No. 61/572,570, Bral.
U.S. Appl. No. 61/630,819, Bral.
U.S. Appl. No. 61/631,416, Bral.
U.S. Appl. No. 61/631,679, Bral.
U.S. Appl. No. 61/632,957, Bral.
http://www.ncbi.nlm.nih.gov/pmc/articles/PMC3001531/ Dec. 14, 2010, Reducing the Pain of Childhood Vaccination. Title: 7, Tactile Stimulation, under Heading: Injection Procedur.

* cited by examiner

Fib. 1a

MEANS AND METHOD TO INVADE SKIN, MUCOSA, AND UNDERLYING TISSUES WITH LITTLE OR NO PAIN

PRIORITY CLAIM

This application is a Continuation-in-Part of and incorporates by reference U.S. Utility patent application Ser. No. 12/590,658 flied on Nov. 12, 2009, Ser. No. 12/927,136 flied on Nov. 8, 2010, and Ser. No. 13/134,013 filed on May 26, 2011. This application is a continuation-In-Part of U.S. patent application Ser. No. 13/550,826 filed on Jul. 17, 2012.

This application is a continuation-in-Part of PCT patent application: PCT/US2012/039258 filed on May 24, 2012 which claims benefit of U.S. Provisional Application Nos. 61/572,570 filed on Jul. 18, 2011, 61/630,819 filed on Dec. 20, 2011, 61/631,416 filed on Jan. 4, 2012, 61/631,679 filed on Jan. 9, 2012, and 61/632,957 filed on Feb. 1, 2012 the disclosures of which are incorporated herein by reference in their entirety.

STATEMENT REGARDING FEDERALLY SPONSORED RESEARCH OR DEVELOPMENT

Not Applicable

THE NAME OF THE PARTIES TO A JOINT RESEARCH AGREEMENT

Not applicable.

INCORPORATION-BY-REFERENCE OF MATERIAL SUBMITTED ON A COMPACT DISC

Not Applicable

BACKGROUND OF THE INVENTION

The prior art literature describes the use of tapping to mitigate the pain of injection. Notable is Helfer Skin Tap Technique in which the nurse administering the injection arranges the injection area to be relaxed, and strikes the vicinity of the injection site firmly with all 5 fingers of the hand about 2 times. Simultaneously with the next strike, she would insert the needle in a dart-like motion into the injection site. Even though the technique is called a skin tap, it looks more like slapping or smacking. There are not many techniques described in the prior art to reduce the pain of injection using tapping, probably because of the following shortcomings. The ones mentioned in the prior art have in common the features of slapping or smacking the recipient simultaneously or immediately prior to the injection. Ms. Helfer also mentions, in a different article, that the strike resembles slapping. In order to calibrate the momentum of the strike that best represents her teachings and gives anesthetic results, I conducted the following two experiments: In the first experiment, I suspended an object weighing 13.4 kg from a pole by a rope of negligible weight. The distance of its center of gravity to the pole was 154 centimeter. I stroked the object at the level of the center of gravity with a horizontal slap and the same firmness as would render anesthetic effects as taught by prior art. I measured the distance the object moved horizontally in the same direction of the slap as the result of the strike. The average of 4 such measurements was 80 mm of travel by the object. In the second experiment, I poured 2.1 litters of water in a cylinder, placed on a flat horizontal surface and with a 235 mm diameter, with a total weight of 2.8 kg, and a center of gravity located 12 cm above the center of the bottom of the cylinder. Depicting the force of a firm tap/slap with all five fingers and the palm of the hand, in a horizontal strike, I was able to just tip the cylinder when the center of the strike was about 33 cm above the bottom of the cylinder. The cylinder was not allowed translational movement. It was only allowed to freely tip over if the tapping forces overcame the gravitational forces. For the sake of clarity, the tapping with this force is called slapping throughout this application. Ms. Heifer also notes that a mere tap by one or two fingers on the injection site is ineffective. In her technique, a dart-like motion of the needle requires a certain amount of manual dexterity—which few people, mostly nurses and care givers have.

Furthermore, it would be impossible to use only one hand to give a painless injection with her technique as one needs to slap with one hand and Inject simultaneously with the other. This would limit the areas on one's body where one's two hands can reach to administer a painless injection. Also slapping may be insulting to some patients. Furthermore, her technique is more geared towards injections administered by nurses and caregivers than for self-injection.

There is a habit by some care givers to lightly tap on or around an injection site generally to pop the vein for the purposes such as intravenous needle insertions. In general, this practice involves 2 or 3 light taps before inserting the needle. The light tapping by itself has no anesthetic effect. Furthermore, even combined with TENS pulses, light tapping needs be performed for several seconds to be effective. 2 or 3 light taps have no anesthetic value. Also, the injection is administered simultaneously or immediately after the light tapping. There is no delay between the tapping and the injection of more than one or more seconds.

According to prior art, if there is a delay between the tapping and injection, then there is no anesthesia. The reason for the need to simultaneously inject is what the Gate theory is based on, namely, that the afferent Impulses arising from the tapping of the injection area cause the nervous system to shut down the sensory gate that would otherwise allow the pain sensation of the injection to reach the brain. So the injection pain goes unnoticed. However, once the afferent impulses indicating a tapping sensation stop reaching the nervous system in adequate quantity, the gate opens and can transfer the pain of injection to the brain. The amount of time it takes to process the information about the tapping sensation is a fraction of a second within which one needs to inject. This is all according to the prior art. This inventor has discovered that the anesthetic effects of slapping may last up to about 4 seconds.

One requires much manual dexterity to be able to slap and inject simultaneously. As mentioned, there is only a window of a short time between slapping and completion of the otherwise painful needle insertion. So a relatively rapid needle insertion is a must. Also the timings of the slap and the needle insertion must coincide accurately. There s a need to find a solution so that the injection can be performed slowly and carefully several seconds up to a few minutes alter the tapping.

The literature describes that rubbing the injection site prior to the injection site reduces the injection pain. I conducted a research to study the effects of rubbing on injection pain. In doing so, I rubbed the injection site 10 times at a speed of about 1 inch per second with a force of 15 ounces on different body parts such as the abdomen and the loins and then attempted to insert a needle. The needle pain was not noticeably any less than without rubbing the injection area. I would conclude that rubbing the injection area prior to the injection prepares the recipient psychologically. A good example would be a person tanning in the sun on whom cold water is splashed. His reaction would be different if, before the splash, he first gently applied some water on his body than if the cold water suddenly and directly came in contact with his sun-heated dry body. He feels the cold water in either case. But if he applies water on his body before the splash, he is more prepared. I believe rubbing the injection site in conjunction with an injection has a similar psychological effect without significantly diminishing the sensation of pain of an injection. However, by combining TENS and rubbing. I was able to consistently obtain painless or near painless needle insertions. In my experiments, I used #30-22 gage needles, but other needle sizes can also be used. The teachings of this invention actually minimize or remove the pain of injection.

Coulter, in his US patent application #: 20040015188, mentions that applying TENS to the vicinity of the injection area lowers or prevents the perception of injection pain. I was unable to reproduce this result using one group of electrodes including only 2 electrodes. Even Coulter in his US patent app. #: 20050149145, mentions that TENS alone has "a poor record of success" in alleviating the injection pain. And "The current general designs of the signal application electrodes used for TENS as well as the type of TENS generating and control units are inappropriate for" bringing about local anesthesia by applying TENS through two groups of electrodes. According to the Gate theory, TENS alone delivered by one group of electrodes should have some anesthetic properties against an injection pain. I also mentioned in the US patent application: 20110112477 that delivering a TENS current alone to the vicinity of the injection site reduces or prevents the injection pain. However, these results cannot be verified clinically. TENS alone does not noticeably reduce the pain of injection. TENS pulses merely provide a tingling sensation that mimics small pin pricks. The following analogy would help me explain this better. A bright light in the dark is very noticeable. If there are lit candles in the background, they reduce the contrast between light and dark. The bright light will therefore be less glaring. The Intensity of the bright light, however, does not diminish when lighting candles in the background. That is what TENS does. It reduces the contrast between the moment before the needle touches the skin and the injection pain. One however feels the injection pain generally with the same intensity nonetheless. Upon following the teachings of this invention, one can dim the light or completely extinguish it. The pain of injection is not masked. It is alleviated. One cannot obtain this phenomenon by applying TENS alone in a meaningful way.

In the present invention, even when the recipient observes the needle being inserted into his/her skin, the pain of the needle is either significantly reduced or completed avoided.

In US app. #: 20050149145 a means and method are disclosed that use TENS to bring about local anesthesia. However, the means and the method mentioned are ineffective and have an adverse effect on the recipient's skin health.

Vibration is produced by a mechanical oscillation of a moving apparatus in a back-and-forth or rotational movement at a relatively high frequency. Due to the high frequency of back-and-forth or rotational movement, the moving apparatus has a very short time to travel in one direction. Therefore, the strokes are very short. Also noteworthy is the flexible nature of the skin and the underlying soft tissue. Since the soft tissue is pliable, it does not transfer the forces of vibration, exerted in very short strokes, internally in deeper tissues as well as the forces of tapping that have a much longer path of stroke. It would therefore be more difficult to stimulate the sensory nerves to actuate the Gate mechanism with vibration than with tapping.

In addition, vibration adds bulk to the method of painless injection because you need a mechanical vibrating system and a battery to power it (outlet electricity is not used in devices coming in contact with one's body due to the risk of electrocution). However, due to the difficulty to stimulate the sensory nerves to actuate the Gate mechanism with vibration, one would need even a more powerful vibrating system. That adds even more bulk to the method of using TENS and vibration to mitigate the injection pain. Compare that to the method of combining TENS with manual tapping or rubbing that requires no bulk for physical stimulation. There is a need for a better means and method to reduce the bulk for painless injections using vibration in conjunction with electrical impulses.

There are many ways to alleviate the pain of a skin puncture. US Patent Application, 20090004628, discusses many of them and enumerates their disadvantages as 1) Pain control achieved is slight to moderate, 2) Method requires excessive time, and 3) Method is awkward.

In US patent application 20080109049, two electrodes apply waveform electricity to the vicinity of a puncture site to alleviate the pain of a skin invasion. Without the use of a physical stimulation, the electrical application is of limited benefit in reducing the pain as my results show. Furthermore, sometimes it is needed to extend the anesthetic effects after the termination of electrical stimulation, the physical stimulation, or both. Also, there is a reference to moving the electrodes from one site to another. This movement does not provide a rubbing sensation as it merely provides for carrying the electrode from one location and placing it in another.

In US patent application 20020147446, there is a reference to moving the electrodes on the tissue for electrosurgical procedures. This procedure is meant to burn the tissue and is not anesthetic.

In US patent application 20100030299, the electrodes are moved without losing contact with the skin on the head to apply electricity to treat a headache.

In US patent application 20040230227 and U.S. Pat. No. 6,708,060, electrodes are moved over the skin without losing contact therefrom in order to ablate the stratum corneum and open micro channels for drug transport across the skin.

In US patent application 20020193861, electrodes are moved over the skin without losing contact therefrom in order to stimulate the living tissue for various therapeutic, analgesic, muscle training, and recreational uses.

In US patent application 20090118789, 2 sets of electrodes are used, one for stimulation of nerves and muscles, and the other, that is applied superficially, for preventing the undesirable sensations possibly resulting from the excitation of the subcutaneous receptors by the stimulation current. According to 20090118789, application of TENS currents, when they effectively stimulate the nerves and muscles, also generates an undesirable pain and tingling sensation that its inventor tries to remedy by a second set of electrodes applying a second current to the area.

In US patent application 20040015188, electrodes are attached to a syringe to apply a TENS current for anesthetic purposes. However, as demonstrated in Table 2 below and as Mr. Coulter himself mentions in his subsequent US patent application, TENS alone has a very limited effect, if any, in ameliorating an injection pain. A better method of obtaining local anesthesia is needed to administer a painless injection.

In US20080039829, electrodes are used to heat an anatomical hallow structure for the purposes of tumescent tissue compression.

In U.S. Pat. No. 5,496,363, use is made of TENS only to provide local anesthesia intra-orally or extra-orally. Also a guide for the syringe needle is provided to direct it to the injection site. This design needs the added step of sterilizing the guide between each use as it touches the needle. An improved design is needed to avoid contact between the needle and the electrode so as to obviate the step of sterilization of the electrode between each use.

In U.S. Pat. Nos. 4,676,257 and 4,924,880, again TENS only is the source of intra-oral local anesthesia, but with the added feature of the patient being able to control the electrical intensity.

Attempts have been made to make more pleasant the drawing of blood for example for monitoring the blood glucose level. U.S. Pat. No. 7,386,349 provides a finger receptacle that includes TENS electrodes to provide anesthesia during lancing the finger. Again better designs are needed as TENS alone has limited effect on reducing the pain of a skin puncture. Furthermore, electrodes with larger surface area than those capable of contacting a finger may be more effective to ameliorate an injection pain.

Vetanze U.S. Pat. No. 7,503,927 applies heat.

Petitt in US2008/0125842 describes the application of a cold medium to control chronic pain by reducing inflammation.

BRIEF SUMMARY OF THE INVENTION

Use is made of sensation of electrical shock and physical stimulation of the skin near the injection site to effect painless or near painless injections.

It is the aim of this invention to provide a method of giving painless injection that 1) does not require slapping the recipient. A mere tapping with one or two fingers would suffice. 2) does not require a dart-like motion of the needle 4 into the soft tissue. A careful slow needle insertion would also be painless. 3) can be administered using one hand.

It is another aim of this invention to provide a method of giving a painless injection that would also minimize or remove the post-injection soreness even after the electrical and physical stimulations are removed.

It is another aim of this invention to extend the anesthetic effects of slapping, as defined by Helfer, to last more than 4-5 seconds by applying electrical stimulation to the vicinity of the skin 2 puncture.

It is another aim of this invention to provide a method of giving a painless injection employing rubbing the injection area requiring a force as small as 5 ounces or less.

It is yet another aim of this invention to provide a means and method of painless injection consistently for the majority of the world population.

Yet another aim of the invention is to provide a skin puncture means and a method of using same to painlessly puncture the skin while mimicking a human touch.

BRIEF DESCRIPTION OF THE SEVERAL VIEWS OF THE DRAWINGS

The characteristics of the present invention will be better understood by reading the following description, given purely by way of example, and with reference to the accompanying drawings, in which:

FIG. 1a illustrates a barrier that prevents a finger or a tapping mechanism to touch and contaminate an injection site.

DETAILED DESCRIPTION OF THE INVENTION

I conducted many experiments to measure the effectiveness of various methods to administer painless injections. In general, I used a needle 4 with gage 30 unless otherwise indicated. Of course, other gage needles may be used throughout these experiments with similar results. I injected to various body parts including the arm, deltoid, belly, and loins. Injection in other body parts is expected to give similar results. The subsequent injection experiments were delayed a few days until the pain of the prior injection subsided so as not to interfere with the result of the next injections. Most experiments were performed on one subject. Only a limited number of subjects participated in this study. I found 20% of the population to be immune to the anesthetic effects of the methods and means of this invention. The results of the experiments on this 20% are not recorded in the following. The main objective of these experiments was to measure the sensation of pain at the time of needle 4 penetration and also the Post-Injection pain-PIP. After the injection, there is commonly a sensation of pain that ensues after a few seconds and lasts for as long as many minutes which I call PIP. The various novel methods of painless injection described in this application have been shown to decrease or prevent this pain sensation as well. In the following experiments, a lighter strike (2-finger tapping, or tapping for short) than slapping mentioned above was administered as it is advocated in this patent application to give anesthetic results with the assistance of TENS, Transcutaneous Electric Nerve Stimulation. In order to calibrate the momentum of this strike, I conducted the following two experiments: In the first experiment, I suspended an object weighing 1.73 kg from a pole with a string of negligible weight. The distance of its center of gravity to the pole was 167 centimeter. I stroked the object, with a horizontal strike, at the level of the center of gravity with the same firmness as would render anesthetic effects as taught in this application, namely the force of a tap by one or two fingers. I measured the distance the object moved horizontally in the same direction as the strike and as the result of the strike. The average of 4 such measurements was 160 mm of horizontal travel by the object. In the second experiment, I poured 150 grams of water in a cylinder weighing 60 grams with 74 mm outside diameter, with a total weight of 210 grams, and an overall center of gravity of 40 mm vertically above the center of the bottom of the cylinder—when the cylinder contains 150 mm of water and is positioned on a flat horizontal surface. Depicting the force of a tap with one or two fingers needed to cause anesthesia when combined with TENS, I was able to just tip the cylinder when the center of the horizontal strike was about 172 mm above the bottom of the cylinder. The cylinder was not allowed translational movement. It was only allowed to freely tip over if the tapping forces overcame the gravitational forces. For the sake of clarity, throughout this application I refer to this force/momentum as 2-finger tapping, or tapping for short. This force/momentum was needed for the specific individuals in the experiment. It may vary from an individual to the next depending on many factors such as sensitivity to tapping, electricity, body water and electrolyte content, any medicine they take presently or took in the past, skin 2 sensitivity, etc. However, it is less than the force of slapping.

I measured the pain sensation to be from 0-10, 0 signifying no pain and 10 the normal pain of injection. Throughout the experiments, the needle 4 insertion was discontinued if the normal pain of injection was perceived. It is possible to reasonably vary one or more parameters of the experiments below and still obtain similar results as taught in the application. Throughout the experiments, use was made of commercial grade TENS electrodes, with conductive adhesive that comes in contact with the skin and an insulating backing that supports the conductive adhesive, that were stationed on the recipient's body. However, various other electrodes can also be used for this purpose.

I then measured the pain of a needle 4 stick on various body parts without any anesthetic help such as a physical or electrical stimulation of the injection site or its vicinity. The pain results are recorded as:

TABLE 1

No stimulation with injection

| Attempt | #1 | #2 | #3 | #4 | #5 | #6 | #7 | #8 | #9 | #10 | #11 | #12 |
|---|---|---|---|---|---|---|---|---|---|---|---|---|
| Pain Level | 2 | 10 | 10 | 10 | 10 | 10 | 10 | 10 | 10 | 5 | 10 | 10 |

Then, I measured the pain of a needle stick with only a prior electrical stimulation by a TENS device 9. Throughout the experiments in this application, the frequency of the TENS device 9 was set at 16 Hz, the width at 160 microsecond, and the amplitude at the highest comfortable level. However, many combinations of the TENS variables, as well as the electrical stimulations before, during, and after the injection, as well as various durations thereof, could give similar results.

In one experiment, I applied TENS to the vicinity of the injection site for the indicated number of seconds, inserted the needle, and then stopped the TENS pulses after 3 seconds. I recorded the pain level for each try, as well as the length of the needle insertion, the PIP, and how long after the injection the PIP started. The results are as follows.

TABLE 2

TENS ONLY

| TENS duration | Pain level | Insertion Length | PIP | How many seconds after injection PIP started |
|---|---|---|---|---|
| 18 | 10 | 1 | NA | NA |
| 20 | 10 | 1 | NA | NA |
| 25 | 10 | 1 | NA | NA |
| 30 | 10 | 1 | NA | NA |
| 35 | 3 | 11 | 1 | 5 |
| 40 | 7 | 5 | 3 | 30 |
| 45 | 10 | 2 | 5 | 2 |
| 50 | 8 | 5 | 3 | 25 |
| 55 | 10 | 1 | NA | NA |
| 60 | 10 | 1 | NA | NA |

Then I measured the pain of needle insertion in conjunction with the method advocated by the prior art. There were three firm taps resembling a slap about 1-2 seconds apart with all 5 fingers and the palm of the hand around the injection site. Simultaneously with the $3^{rd}$ slap, the needle was inserted in a dart-like manner. The force/momentum of the slap was approximately as the momentum of the slapping calibrated above.

TABLE 3

Method: Slap, Slap, Injection + Slap together.

| Attempt | Pain Level | Insertion Length | PIP | PIP started after how many seconds |
|---|---|---|---|---|
| #1 | 0 | 25 mm | 6 | 30 |
| #2 | 0 | 25 | 7 | 25 |
| #3 | 1 | 26 | 9 | 10 |
| #4 | 0 | 26 | 5 | 10 |
| #5 | 2 | 23 | 7 | 15 |

Next, I used tapping only, with 2 fingers, and exerting the amount of force/momentum approximately as calibrated above without the use of electric pulses. I tapped the injection site vicinity with 2 fingers at a rate of about 1 tap per second for X seconds. Again, one can change reasonably the various parameters such as the duration, the rate, and the force of tapping and the insertion length to also obtain similar results. The following results were obtained:

TABLE 4

Method: Tap with 2 fingers, 1 tap/sec for X seconds, then inject.

| X | Pain Level | Insertion Length | PIP | PIP started after how many seconds |
|---|---|---|---|---|
| 30 | 1 | 10 | 5 | 10 |
| 35 | 10 | 1 | 3 | 15 |

TABLE 4-continued

Method: Tap with 2 fingers, 1 tap/sec for X seconds, then inject.

| X | Pain Level | Insertion Length | PIP | PIP started after how many seconds |
|---|---|---|---|---|
| 40 | 10 | 1 | 5 | 5 |
| 45 | 9 | 1 | 3 | 15 |
| 50 | 10 | 1 | 3 | 40 |
| 55 | 9 | 1 | 5 | 25 |
| 60 | 10 | 1 | 5 | 35 |

I then measured the injection pain after rubbing the injection area 10 times at a speed of about 1 Inch per second with a force of about 9-15 ounces and then attempting to insert the needle.

TABLE 6

Method: Rubbing 10 times with 9-15 ounces and inject w/o TENS

| Attempt | Pain Level | Length of Needle 4 insertion |
|---|---|---|
| #1 | 0 | 11 mm |
| #2 | 1 | 5 |
| #3 | 10 | 1 |
| #4 | 10 | 1 |
| #5 | 10 | 1 |
| #6 | 10 | 2 |
| #7 | 9 | 1 |
| #8 | 8 | 2 |
| #9 | 9 | 2 |
| #10 | 10 | 1 |
| #11 | 10 | 1 |

In the following, the results of the experiment to measure the pain of injection after applying pressure to the injection site are recorded.

TABLE 7

Method: Pressure and then inject.

| Attempt | Force | Duration | How many times before injection | Pain level | Insertion Length |
|---|---|---|---|---|---|
| #1 | 15 oz | 7 sec | 1 | 1 | 11 |
| #2 | 15 oz | 7 sec | 1 | 10 | 0 |
| #3 | 15 oz | 10 sec | 1 | 10 | 0 |
| #4 | 1.6 lb | 1 sec | 9 | 3 | 11 |
| #5 | 15 oz | 1 sec | 9 | 10 | 1 |
| #6 | 15 oz | 1 sec | 9 | 10 | 1 |

These results show that electrical or physical stimulation alone has limited ameliorating effect on injection pain. In the following, the effects of combining electrical pulses with tapping, rubbing, or applying pressure are recorded.

The next experiment was performed by applying TENS pulses and tapping together for 15 seconds, then stop tapping but continue TENS for an additional X seconds, and then inject, followed by stopping TENS after 3 seconds. The pain level, the insertion length, PIP, and the onset of PIP were recorded.

TABLE 8

Method: TENS + Tap 15 sec, TENS for X sec, Inject

| X | Pain level | Insertion Length | PIP | Highest PIP started after how long? |
|---|---|---|---|---|
| 3 | 3 | 20 mm | 0 | — |
| 5 | 5 | 25 | 0 | — |

TABLE 8-continued

Method: TENS + Tap 15 sec, TENS for X sec, Inject

| X | Pain level | Insertion Length | PIP | Highest PIP started after how long? |
|---|---|---|---|---|
| 10 | 1 | 25 | 0 | — |
| 15 | 1 | 25 | 0 | — |
| 20 | 1 | 25 | 1 | 5 seconds |
| 25 | 2 | 25 | 1 | 10 |
| 30 | 3 | 10 | 2 | 15 |

In a different experiment, TENS and 2-finger tapping were applied to the injection site for 20 seconds, stopped tapping but continued TENS for an additional X seconds, and then Inject with a 22 gage needle with an insertion length of 25 mm.

TABLE 9

Method: TENS + tap for 20 sec, TENS for X sec, inject with #22, 25 mm.

| | X | | | | | |
|---|---|---|---|---|---|---|
| | 5 | 10 | 15 | 20 | 25 | 30 |
| Pain Level | 0 | 1 | 0 | 1 | 1 | 0 |

In the following experiment, I applied TENS and 2-finger tapping together for X seconds and stopped tapping, stopped TENS after Y seconds, delayed injection for Z seconds, and then injected with a #22 gage needle with a penetration depth of 25 mm.

TABLE 10

Method: TENS + Tap, Delayed Injection

| X | Y | Z | Pain level |
|---|---|---|---|
| 15 | 3 | 7 | 0 |
| 15 | 2 | 13 | 0 |
| 15 | 4 | 16 | 1 |
| 15 | 3 | 22 | 1 |
| 15 | 2 | 28 | 1 |

I also experimented with the method of applying a rubbing sensation together with an electrical stimulation to the vicinity of the injection site prior to injection. I first applied TENS to and rubbed the area 10 times at a speed of about 1 inch per second with a force of about 9-15 ounces and then attempted to insert the needle 4 in about 3 seconds after the rubbing was terminated. In about 3 seconds after the injection, I terminated the TENS application. The resulting pain sensation is recorded in the following:

TABLE 11

Method: Rubbing + TENS, then inject.

| | Method | | | | | | | | | | |
|---|---|---|---|---|---|---|---|---|---|---|---|
| | #1 | #2 | #3 | #4 | #5 | #6 | #7 | #8 | #9 | #10 | #11 |
| Pain Level | 0 | 10 | 1 | 0 | 1 | 0 | 2 | 10 | 2 | 2 | 2 |
| Insertion Length | 11 | 0 | 11 | 11 | 11 | 11 | 11 | 1 | 11 | 11 | 11 |

In another experiment, I applied TENS pulses to the injection area through 2 electrodes for 15 seconds, then while continuing to apply TENS, I applied pressure with the recorded force to the injection area in between the electrodes for the recorded duration and number of times. The resulting pain sensation is mentioned for each experiment.

TABLE 12

Method: Pressure + TENS, Inject

| Attempt | Force  | Duration | Number of times | Pain level | Insertion Length |
|---------|--------|----------|-----------------|------------|------------------|
| #1      | 15 oz  | 7 sec    | 1               | 0          | 11 mm            |
| #2      | 15 oz  | 10 sec   | 1               | 10         | 0                |
| #3      | 15 oz  | 10 sec   | 1               | 1          | 11               |
| #4      | 1.6 lb | 10 sec   | 1               | 8          | 5                |
| #5      | 1.6 lb | 1        | 9               | 1          | 11               |
| #6      | 15 oz  | 1        | 9               | 10         | 1                |
| #7      | 15 oz  | 1        | 9               | 3          | 11               |
| #8      | 9 oz   | 1        | 5               | 4          | 11               |
| #9      | 9 oz   | 1        | 5               | 10         | 1                |
| #10     | 9 oz   | 1        | 5               | 10         | 1                |

In a different experiment, I first applied TENS for X seconds, then TENS and 2-finger tapping for Y seconds, stopped tapping and Injected after 3 seconds, and then stopped TENS after 3 seconds. I then recorded the pain level, PIP, and the onset of PIP.

TABLE 13

Method: TENS for X seconds, TENS + Tapping for Y sec, 3 sec, inject, stop TENS after 3 sec.

| X     | Y     | Pain Level | PIP | Onset of PIP |
|-------|-------|------------|-----|--------------|
| 5 Sec | 5 sec | 2          | 1   | 60 sec       |
| 2     | 3     | 3          | 5   | 2            |
| 2     | 3     | 2          | 1   | 40           |
| 2     | 3     | 10         | —   | —            |
| 2     | 3     | 10         | —   | —            |
| 5     | 3     | 2          | 5   | 1            |

In the following I applied TENS for 2 seconds, then while continuing TENS, I tapped X times. After the termination of tapping, I waited for 2 seconds and injected. Then I stopped TENS 2 seconds after injection.

TABLE 14

Method: TENS for 2 seconds, then TENS + tapping X times, wait for 2 seconds and inject, then stop TENS 2 seconds after injection.

| X       | Pain Level | Insertion Length | PIP | Onset of PIP | Location |
|---------|------------|------------------|-----|--------------|----------|
| 1 Time  | 1          | 7 mm             | 1   | —            | Abdomen  |
| 2 times | 8          | 3                | 10  | 10 seconds   | Abdomen  |
| 3       | 10         | 1                | —   | —            | Abdomen  |
| 4       | 5          | 15               | 1   | 5            | Abdomen  |
| 5       | 10         | 1                | 3   | 10           | Abdomen  |

In the following, I repeated the steps as in the experiment in Table 14, with the exception that the initial TENS application was for a 15 second duration.

TABLE 15

Method: TENS for 15 seconds, tap X times and continue TENS, wait 2 seconds and inject, then stop TENS 2 seconds after injection.

| X       | Pain Level | Insertion Length | PIP | Onset of PIP | Location of Injection |
|---------|------------|------------------|-----|--------------|-----------------------|
| 1 time  | 10         | 1                | 3   | 30 sec       | Loin                  |
| 2 times | 10         | 2                | 4   | 20           | Loin                  |
| 3       | 10         | 2                | 4   | 20           | Loin                  |
| 4       | 10         | 1                | 2   | 2            | Loin                  |
| 5       | 2          | 10               | 2   | 10           | Loin                  |

In a preferred example of the invention, one or more currents, at least one of which is TENS, are applied by two or more electrodes 1 to the skin 2 adjacent to the skin puncture site while physically stimulating—by tapping, rubbing, or vibrating, or applying pressure more than once in the vicinity of the puncture site generally in between or near the electrodes 1 for a required period of a few seconds or more before, during, or after the application of TENS. Using this method, the skin 2 can painlessly or near painlessly be punctured and the underlying soft tissue pierced to a depth of 50 mm or more. Furthermore, the electrodes 1 can be spaced apart as much as 50 mm or more to achieve this result. These electrodes 1 can for example be of the commercial grade commonly used in typical TENS applications such as relieving backaches. I usually obtain satisfactory results by tapping at a rate of 1 to 2 taps per second for about 15-20 seconds, but other rates and durations of tapping may also yield satisfactory results. It may also be necessary to change some or all of the variables, such as rate of tapping, duration of applying physical or electrical stimulation, the force of tapping, rubbing or pressure, etc., related to the teachings of this invention depending on many factors such as the age of the recipient, the body part receiving the injection, the physical and emotional condition of the recipient, etc.

Rubbing the skin 2 area with a force of as little as 5 ounces or less, in conjunction with TENS, can affect local anesthesia for adult human recipients for otherwise painful skin 2 procedures such as a skin 2 puncture, a needle 4 penetration of up to 50 mm or more, or epilation. For infants and children this force may be less. However, without TENS, the pain of skin 2 puncture is felt more or less as severely as without rubbing.

Applying a pressure of 9 ounces or more in conjunction with TENS, one or more times, was not as effective to result in local anesthesia. It was however helpful to somewhat reduce the injection pain as shown in table 12.

The results of the above experiments show that without electrical stimulation, physical stimulation in the form of 2-finger tapping, rubbing, or applying pressure to a skin 2 puncture site has a limited effect, if any, in ameliorating the pain of injection. Furthermore, the combination of electrical stimulation and physical stimulation in the form of tapping, rubbing, vibrating, or applying pressure results in an anesthetic effect that lasts a few seconds up to a few minutes after the termination of the electrical and/or physical stimulation. These results can be obtained if electrical and physical stimulations are applied simultaneously, or one after the other. For example, the physical stimulation is applied first for a period of time, e.g., 15 seconds, and then during or at the Conclusion of or a short time (ranging from 1 to several seconds) after the conclusion of these 15 seconds an electrical stimulation is applied to the vicinity of the skin 2 puncture site. The electrical stimulation for example in the form of TENS for example for a period of 16 seconds is applied to the vicinity of the skin puncture site, during, at the conclusion of, or after which the skin 2 is punctured at the skin puncture site with little or no pain, as shown in Tables 8, 9, 10, 11, and 12. This inventor has discovered that it is possible to obtain local anesthesia if a physical stimulation applied to the vicinity of the skin puncture site is followed by an electrical stimulation even after the physical stimulation is terminated as long as the electrical stimulation is not terminated before the skin puncture by more than a few minutes. Needless to say, the anesthetic effects are obtained if the electrical stimulation continues during the skin puncture. For example, one can tap in the skin puncture site or the area adjacent to it, then place a plurality of electrodes 1 that apply TENS to the vicinity of the skin puncture area without further tapping, and then proceed with a painless skin puncture. Similarly, injections can be administered painlessly one second, two seconds, five seconds or more after rubbing is terminated. Similar results can be obtained after the termination of vibration. After applying vibration and TENS for an appropriate amount of time, injections can be administered painlessly with a delay of as much as one minute or more after the termination of vibration. Also after applying compressed gas and TENS for an appropriate amount of time, injections can be administered painlessly with a delay of as much as one minute or more after the termination of applying compressed gas to the injection area. In all the above examples, local anesthesia lingers on after the termination of physical stimulation even if the application of TENS is also terminated, although in my experience, maintaining the application of TENS on the skin at least till injection time enhances the local anesthesia.

Therefore, no simultaneous injection along with any of the mentioned physical stimulations is needed. This would reduce the risk of accidental needle sticks. It would not be necessary to rapidly insert the needle to reduce or prevent the injection pain. It is possible to aim the needle carefully and inject slowly to further reduce the risk of an accidental needle stick to the operator, to prevent the chance of a needle getting bent due to the high speed impact of the needle to the recipient's soft tissue. The significance of the careful aim of the needle is emphasized since one needs to stay clear from the electrodes 1 that apply electricity to the vicinity of the injection site. If moving the needle 4 rapidly, the operator may accidentally hit the electrodes 1 before inserting the needle 4 into the recipient's soft tissue. Since a slow and careful needle 4 insertion can accommodate a painless or a near painless injection, thinner needles are possible to use with the resultant more comfort associated with thinner needles. This inventor also noted that the post-injection pain/soreness experienced as overall pain of injection is much less with TENS+tapping than with tapping/slapping alone. In experiments performed to confirm this finding, TENS was stopped one or more seconds after the injection. Similar results can be obtained if the application of TENS pulses stops before or while the injection is given. Also noteworthy is the fact that since the anesthetic effects of the aforementioned method linger on for a while, the immediate discomfort of a painful injectable medicine is reduced or prevented. This will allow the medicine to dissipate, or an anesthetic solution, such as lidocaine, that was pre-mixed with the injected medicine to affect a longer-lasting and more profound anesthesia before the anesthesia from the electrical and physical stimulations wears off.

The experiments conducted by this inventor show that without the use of TENS, the anesthetic effects of slapping may last up to 4 seconds, contrary to the teachings of the prior art that based on the Gate theory would require the slapping to occur simultaneously or just prior to the injection. Moreover, when TENS is used, in conjunction with 2-finger tapping painless or near painless injections can be obtained up to more than 30 seconds or more after the tapping stops. The test results are in Table 10.

Figure 10:
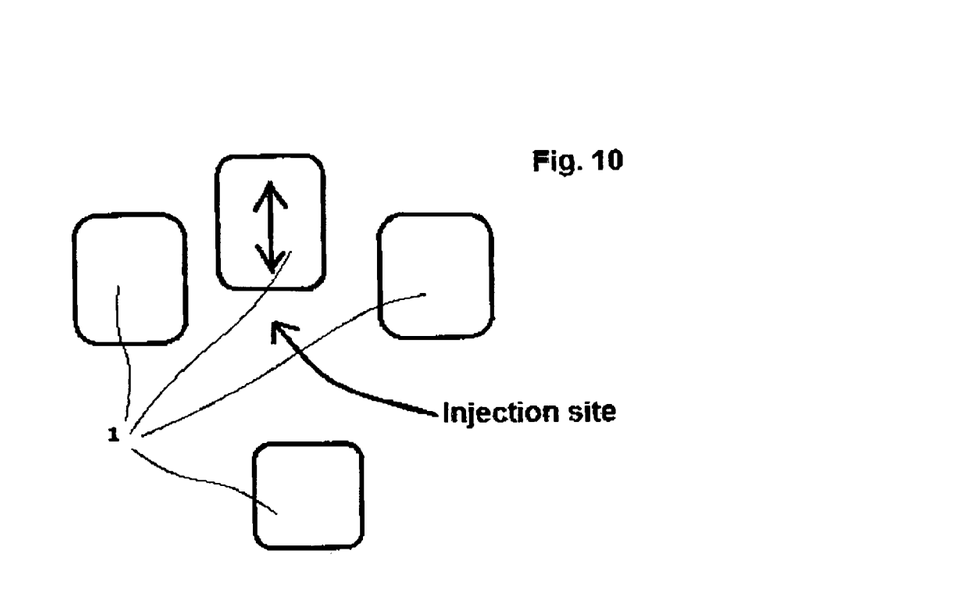
FIG. 10 illustrates a preferred positioning of 4 electrodes near an injection site where one electrode rubs on the skin.

In a method of obtaining local anesthesia, rubbing is performed before, during, or after applying electricity via a plurality of electrodes 1 to the vicinity of skin 2 puncture site. In my experience, rubbing performed before and during application of electricity is more effective than applying it after the termination of the electrical stimulation. One may rub the skin 2 while the electrodes 1 are stationary, or at least one electrode is moving against the skin 2 of the recipient and thereby providing a rubbing sensation. This design has the added advantage that the one or more electrodes 1 in their path of movement apply TENS to more sweat gland end hair follicles—through which one transmits electricity to the underlying tissues—and nerve endings and branches some of which would otherwise transmit the pain sensation to the brain. Therefore smaller electrodes 1 can be used to effect anesthesia before the skin 2 puncture. This is helpful when, say, an auto-injector such as an insulin pen includes a plurality of electrodes 1 for example on one of its sides that is generally flat. Smaller electrodes 1 allow a more compact design on the auto-injector. I was able to obtain a more profound anesthesia when I applied 2 electrodes 1 on the skin with about 2 inches of space between them, applied another electrode 1 to the skin positioned to the side of and generally in between the first 2 electrodes 1, and rubbed a fourth electrode 1 in between the first 2 electrodes 1. FIG. 10. Of course, different shape, arrangement, and number of electrodes 1 as well as spaces between the electrodes 1 can enhance the local anesthesia on the skin. At least one of the electrodes 1 can be applying the rubbing to the skin, or all of the electrodes 1 may be stationary with respect to the skin. In the latter case, another object may apply rubbing to the skin.

Figure 9:
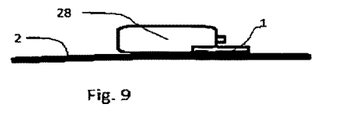
FIG. 9 shows a pressurized gas can positioned to generally blow air towards the skin and connected to one or more electrodes that face the skin for applying electricity to the skin.
Figure 9A:
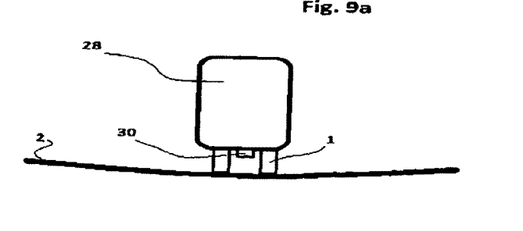
FIG. 9a shows a can including 2 electrodes that when pressed to the skin blows gas to the skin through a nozzle.

In a method of obtaining anesthesia, TENS is applied to the vicinity of the area being anesthetized and a disinfectant preferably with a relatively low boiling point such as alcohol is applied to the injection area before the injection which also acts a cooling agent. One or more burst of compressed gas are applied to the disinfectant to 1) exacerbate the cold sensation on the skin 2, 2) blow away any remaining antiseptic from the skin 2 which would otherwise cause a burning sensation upon injection, 3) cause the physical sensation felt by the blowing gas to help decrease or prevent the pain, and 4) and mask the sensation of electrical shock from TENS. For example, a can 28 containing pressurized gas such as air may include one or more electrodes 1 that can come in contact with the recipient's skin 2, FIG. 9. As the can 28 blows air and the electrodes 1 apply electricity to the skin 2 at the puncture site or its vicinity, local anesthesia is obtained in the vicinity of the puncture site. In a preferred embodiment of the Invention, when one presses one or more electrodes 1 included in a can 28 to the skin 2, one activates the TENS application to the injection area through the electrodes 1. In another example, one also actuates the release of one or more bursts of compressed gas to the injection area through one or more nozzles 30. A microprocessor may also coordinate the sequence, duration and strength of the bursts of compressed gas and TENS application. In a similar embodiment of the invention, the gas itself may be cold, for example it may include ethyl chloride, a vapo-coolant, which is applied on the skin near the injection site.

In another example of the invention, a liquid such as a disinfectant is rubbed dry on the skin. The rubbing can be performed by at least one electrode 1 or another object. The rubbing can be in conjunction with applying compressed gas to the skin or it may be performed without the assistance of compressed gas. However, rubbing is always applied at least before, during, or after applying electricity to the skin, preferably in the form of TENS.

Figure 10A:
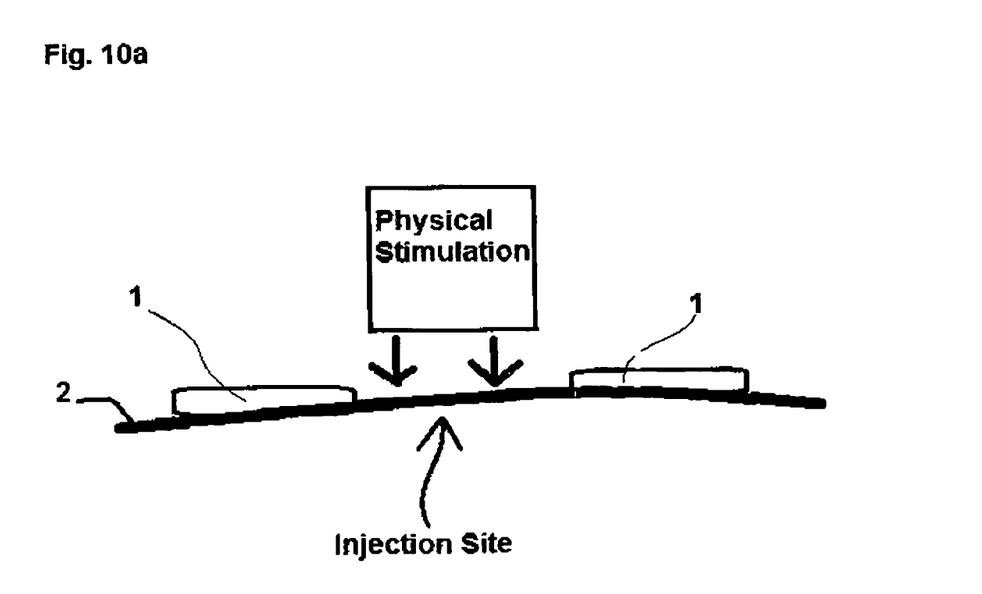
FIG. 10a shows a diagram of applying TENS and physical stimulation to the vicinity of the injection site.

In one preferred embodiment of the invention, a skin puncture means 5 includes a plurality of electrodes 1. One can apply physical stimulation in the vicinity of the skin 2 puncture site, then place the electrodes 1 included on the skin puncture means 5 near the skin 2 puncture site to apply an electrical stimulation such as TENS, and then use the same skin puncture means 5 for a painless skin 2 puncture, FIG. 10a. Furthermore, in one example of the invention, one can use the same skin puncture means 5 to apply physical stimulation before or simultaneously with the electrical stimulation.

This proves important. In the present invention, since the anesthetic effects of the inventive method linger on for some time, it is possible to first apply the physical stimulation and then inject with the same hand. This is in contrast to the prior art that requires a physical stimulation simultaneously with or immediately after needle 4 insertion necessitating the use of both hands. Now, it would be possible to administer injections painlessly to one's self, for example, in one's arm, deltoid, and gluteus or if one needs to grab the tissue before injecting. In an example of the Invention, the skin puncture means 5 further includes a marker 22 projecting out of the body of the skin puncture means 5 that can make an impression on the skin preferably delineating the area of the skin that can be punctured. After applying a disinfectant on the skin, such as alcohol, the injection site should not come in contact with objects such as the electrodes 1 that may contaminate it. The marker 22, for example in the form of a circle, can show where the skin has not come in contact with these objects wherein one can safely puncture the skin 2. The marker 22 can make in impression on the skin by merely pressing on it, or print on it preferably by a disappearing ink.

Figures 5, 6:
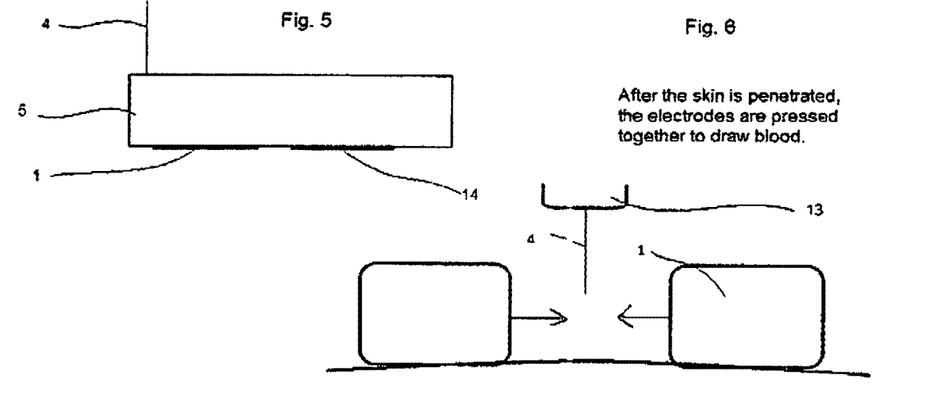
FIG. 5 exhibits a skin puncture means including one electrode and one rubbing means on one side of said skin puncture means and a needle projecting from another side of said skin puncture means.
FIG. 6 shows two electrodes pressed towards each other after a skin puncture to draw blood.

In a different example of the invention, in order to minimize the chance of an accidental needle stick in one handed skin punctures, the needle 4 extends out of the syringe 6 from the opposite side where the plurality of electrodes 1 are located, FIG. 5. Therefore, during physical and electrical stimulations, the needle 4 is pointing away from the body. Then, the operator simply turns the syringe 6 so the needle 4 points towards the skin 2 puncture area, and painlessly puncture the skin 2.

A human touch emits an electrical current. The literature in prior art describes that rubbing and applying pressure to the injection site reduces the injection pain. There are experiments performed that confirm this, even though in my experiments this pain reduction was minimal or not discernible. At any rate, in order to mimic the human touch, the rubbing and application of pressure in the area of the skin 2 puncture is performed by at least one of the plurality of electrodes 1 situated on the skin 2 puncture means.

In a specific example of the invention, one or more electrodes 1 are placed on the recipient's skin 2. The electrodes 1 are then tapped with an adequate force and an adequate number of times. Since the tapping force is dissipated throughout the electrodes 1, more force or momentum than exerted by 2-finger tapping may be needed. The electrodes 1 may apply electricity before, during, and/or after applying tapping to the skin 2. The needle 4 is then inserted generally in between the electrodes 1 into the skin 2 to painlessly or near painlessly administer an injection.

Figure 1B:
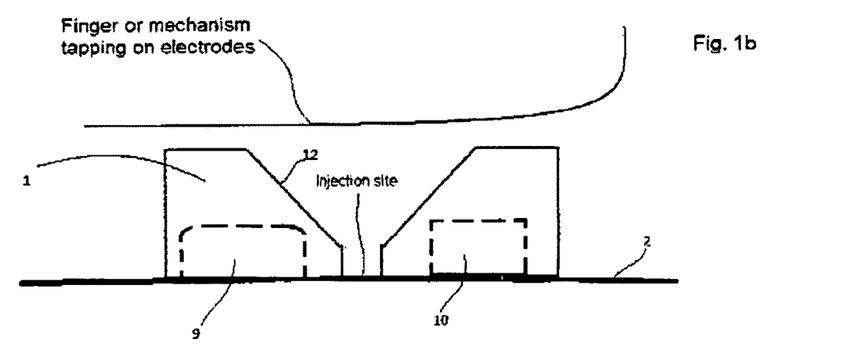
FIG. 1b shows 2 barriers with added thickness to prevent the contamination of the injection site between them.

In an example of the invention, at least one barrier 21, placed on the skin 2, may transfer the physical stimulation such as vibration, tapping, or pressure, and shield the inject ion site and prevent the fingers or a mechanism that applies a physical stimulation to come in contact with the injection site and thereby contaminating it, FIG. 1a. The skin 2 may have been previously disinfected, or the barrier 21 may have a disinfectant surface that comes in contact with the skin 2 to disinfect the skin for injection. In one example of the invention, the barrier 21 can be removed before the injection to expose the disinfected skin site. The barrier 21 may at least significantly fit between at least two electrodes 1. The barrier 21 may further have at least one raised surface to guide at least one electrode 1 to the vicinity of the injection site to be placed in proper contact with the skin 2. The barrier 21 may also be at least partially electrically conductive so as to transfer the electric current from at least one electrode 1 to the skin 2 without removing the barrier 21 first, ensuring that none of the electrodes 1 contaminate the injection site. Also, if there are at least two electrodes 1 positioned near each other, there is a chance that they will transfer electricity to the same electrically conductive barrier 21, thereby shorting the circuit and jeopardizing the anesthetic aim of applying electricity to the skin near the injection site. In order to avoid this, the barrier 21 can be compartmentalized into two or more electrically conductive sections 24, each electrically segregated from the other sections 24, FIG. 1a.

After anesthetic steps are taken to apply physical stimulation and electricity, it may be necessary to remove the barrier 21 to puncture the skin 2 in the area that was previously disinfected and shielded by the barrier 21. In order to demarcate the shielded area of the skin 2 and to show where the disinfected area of the skin 2 is available for an injection or other skin puncture, at least one barrier 21 may leave a mark by an ink, preferably disappearing after a short time on the skin 2 area it is shielding. In another example of the invention, at least one barrier 21 has at least one marker 22 that presses against the skin 2 and temporarily makes an impression on the skin 2 demarcating where the skin was shielded and is therefore sanitized for puncture.

In another example of the invention, one or more barriers 21 are not necessarily removed from the skin 2 before the skin puncture. Instead, they are thick enough to prevent a tapping finger or a mechanism to come in contact with the injection site located near at least one barrier 21, and preferably generally between two or more barriers 21. One or more barriers 21 may include at least one electrode 1. One or more barriers 21 may include at least a TENS device 9 or a battery 10, FIG. 1b.

Figures 4A, 4B:
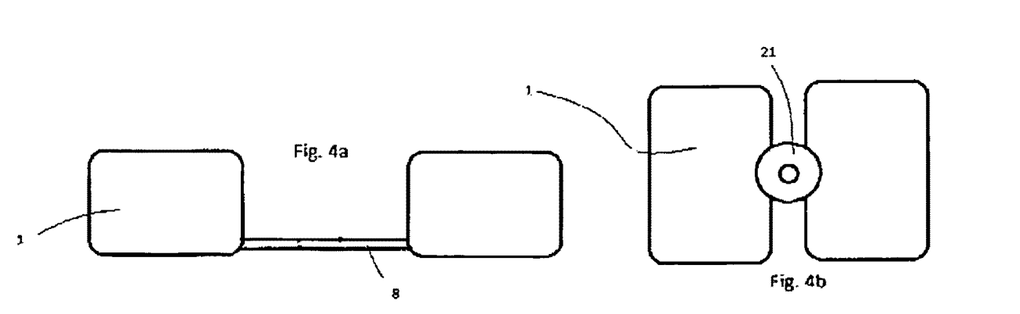
FIG. 4a illustrates 2 electrodes held together by a retaining means that accommodate a needle of a syringe reaching to the injection site in between the electrodes.
FIG. 4b shows a rigid barrier surrounded by 2 flexible electrodes.

In an example of the invention, the electrodes 1 are held together by a retaining means 8 for easy transport and placement on the recipient's skin 2 in appropriate position with respect to each other, FIG. 4a. Furthermore, one or more barriers 21 may adhere to the skin 2 by an electrically conductive adhesive or other retentive means for added convenience.

In addition, one or more barriers 21 may have a rigid characteristic in order to better transfer the impact of a physical stimulation such as tapping or vibration to the underlying skin. However, a rigid substance cannot conform well to the various contours of the recipient's skin. The one or more electrodes 1 are preferably not rigid because they need to conform to the recipient's skin to enhance the electrode-skin interface and the resulting electrical connection necessary for effecting adequate anesthesia. Therefore, in an embodiment of the invention, one or more electrodes 1 are flexible and are connected to and preferably at least partially surround one or more rigid barriers 21 to enhance the sensation of physical stimulation such as tapping or vibration and the transfer of adequate electricity to the skin, FIG. 4b. One or more barriers 21 may have an opening for a sharp object such as a needle 4 to reach the skin 2. Also, one or more flexible electrodes 1 may have an electrically conductive adhesive to adhere to the recipient's skin. In an attempt to bring about a compact design for conveniently transporting a skin puncture means 5, at least one or more flexible electrodes 1 or one or more rigid barriers 21 can, for example, adhere or otherwise attach to one or more surfaces of the skin puncture means 5. When it is time to use them, they are separated from the skin puncture means 5, and placed on the recipient's skin 2.

Figure 4C:
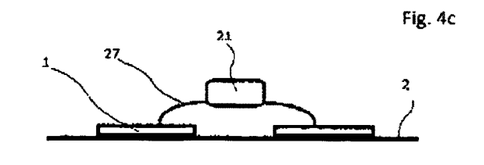
FIG. 4c exhibits a barrier connected to 2 electrodes by 2 springs.
Figure 4D:
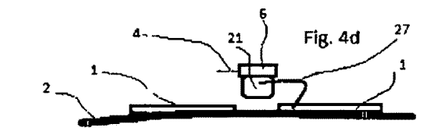
FIG. 4d shows a barrier connected to one electrode and connected to a syringe.

In a preferred example of the invention, one or more barriers 21 can move with respect to one or more electrodes 1 rotationally, translationally, or both, for example by one or more springs 27, FIG. 4c. The one or more springs 27 help maintain one or more of the barriers 21 at a distance from the skin 2. The force exerted by at least one spring 27 may be designed to be as deemed necessary. It may even be zero, i.e., the force exerted on at least one barrier 21 is external, for example a manual force moves the one or more barriers 21 back and forth. The movement of at least one barrier 21 with respect to at least one electrode 1, and by extension the skin 2, helps to improve the sensation of the impact of tapping on the skin 2 since the at least one barrier 21 taps on the skin 2 as a result of the impact it receives, rather than just transferring the impact to the skin 2 while being in contact therewith. Sometimes, when a spring is pressed, it finds a different position than the last time it was pressed. Its position in a pressed state is not consistent. This leads to the barrier 21 being placed in different places on the skin and increasing the chance that the surface of the barrier 21 that comes in contact with the skin 2 may contaminate the injection site. Therefore, it may be preferable to connect the barrier 21 to at least one electrode 1 without the spring 27 to add stability to where the barrier 21 comes in contact with the skin 2. That is, the movement of at least one barrier 21 with respect to at least one electrode 1 may be generally rotational. One or more barriers 21, being connected to one or more flexible electrodes 1 can move against the one or more electrodes 21 by merely flexing the electrode(s). In an example of the invention, at least the Injectable medicine or part thereof is included in at least one barrier 21. The resulting increased combined mass of the barrier 21 enhances the sensation of tapping and the ensuing local anesthesia at or around the injection site. FIG. 4d shows a syringe 6 permanently or separably affixed to a barrier 21.

Figure 2:
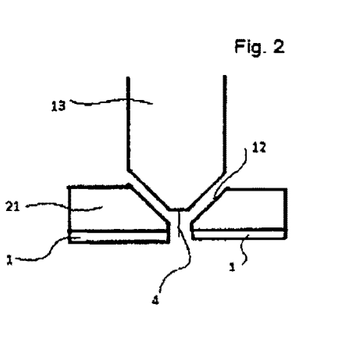
FIG. 2 shows a barrier including a guiding mechanism guiding a lancing device to the skin puncture site.

In a specific example of the Invention, a skin puncture means 5 such as a syringe 6 or a lancing device 13 adapts to one or more barriers 21, FIG. 2. For example, the skin puncture means 5 is guided into the correct positional relationship with respect to the electrodes 1 so as to ascertain that the needle 4 from the skin puncture means 5 does not touch the electrodes 1 on its way to insertion into the recipient.

Figure 3:
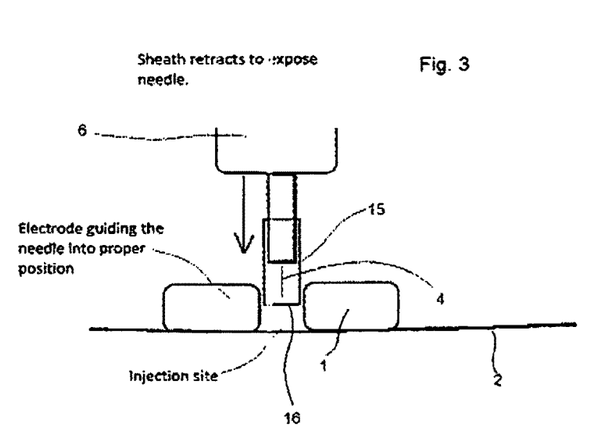
FIG. 3 shows 2 electrodes guiding a sheathed needle of a syringe to the injection site.

For example, a guiding mechanism 12, such as a magnet or a guiding rail, can be used to guide the syringe 6 into position. In an example of the invention, the needle 4 is sheathed inside a sheath 15 that may be extending from the syringe 6. The sheath 15 may be connected to the syringe 6 from one end and be open from the other end. When the needle 4 travels towards the skin 2, the sheath 15 retracts exposing the needle 4 to the skin 2 while protecting the needle 4 from the electrodes 1. In a different variation, the sheath 15 is stationary with respect to the syringe 6 while the needle 4 projects out of the sheath 15 into the recipient's skin 2. The open end of the sheath 15 may be covered by a penetrable membrane 16 such as a rubber sheet to maintain the needle's 4 sterilized conditions, FIG. 3.

One can use a lancing device 13 in another example of the Invention to puncture the skin 2. For example, a diabetic individual required to draw blood for sugar analysis, can place the electrodes 1 on a skin 2 surface of his choice after properly disinfecting the skin 2 puncture area, tap on one or more barriers 21 and/or electrodes 1 a sufficient number of times before, during, or after applying electrical pulses through the electrodes 1 near the skin 2 puncture site, place a lancing device 13 in position on the electrodes 1, puncture the skin 2 nearly or completely painlessly as shown in the tables above (the teachings of this patent application can alleviate the pain of a skin 2 puncture whether it is from an injection or a lance) and draw blood for the glucometer, determine the required insulin dose, prepare the insulin for injection—for example in an insulin pen, place the pen or the syringe 6 in position on the electrodes 1, and proceed with a nearly or completely painless injection. One can tap again on the electrodes 1 that are still in position if needed to provide better anesthesia before a subsequent skin 2 puncture, in this case the injection of insulin.

Sometimes it is necessary to press around the puncture site to draw blood. That is especially true if the puncture is very tiny preventing the blood to flow out on its own. In order to do so aseptically, without removing the electrodes 1, one may press the electrodes 1 towards each other thereby pressing the skin 2 puncture area and drawing blood, FIG. 6. Of course, the electrodes 1 need not touch each other or the blood in the process. This method makes it possible to only puncture one site (the same site is used to draw blood and to inject) on the skin 2 painlessly for the purposes of drawing a blood sample and an insulin injection and thereby minimizing the number of sore areas resulting from the skin 2 puncture on the recipient's body. Of course, the guiding mechanism 12 in the electrodes 1 can be designed to guide the lancing device 13 and the injection needle 4 to different locations if that is preferable.

The guiding mechanism 12 on the electrodes 1 is also helpful in guiding the needle 4 to the skin 2 without touching the electrodes 1 in cases where the physical stimulation comes from vibration, pressure, or rubbing, or when the injector is an elderly or otherwise locks the manual dexterity to manually guide the needle 4 in between the electrodes 1.

In a different example of the invention, after applying a disinfectant to the skin 2 puncture site, a rubbing means 14 as in FIG. 5 rubs the disinfectant until it dries. At the same time it provides a physical stimulation near the puncture site that together with in electric stimulation will have an anesthetic effect. In one example, the rubbing means 14 is preferably located on the skin puncture means 5. The rubbing means 14 may be at least one electrode 1 that applies electric stimulation to the vicinity of the puncture site. This method would ensure that the puncture site and the rubbing means 14 that comes in contact with it are disinfected while providing added convenience of puncturing the skin 2 requiring only one hand. In a specific example of the invention, the rubbing means 14 is so shaped as to spread the disinfectant on the skin 2 to hasten its evaporation.

Figure 7:
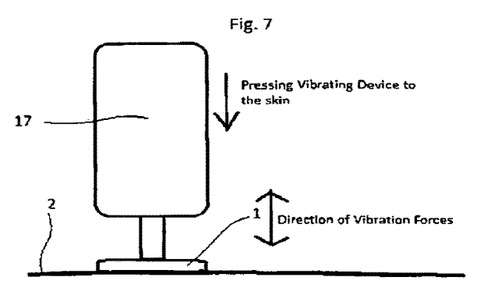
FIG. 7 illustrates a vibrating device generating vibrational strokes and forces generally perpendicular to the skin at the puncture site.
Figure 8:
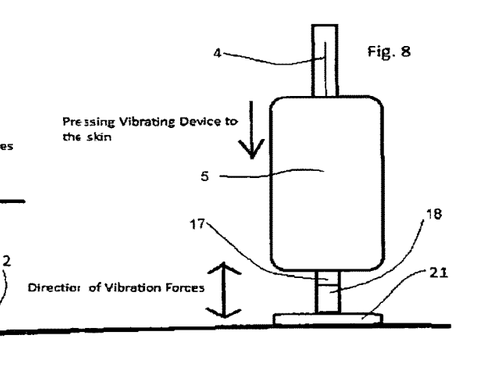
FIG. 8 shows a skin puncture means that includes a vibrating device.

Vallero, in U.S. Pat. No. 8,121,696 discloses a device that includes 2 or more electrodes that supply vibration and TENS to the skin for anesthetic purposes. The two areas in his patent that I would like to improve on in this application are that 1) the electrodes extend out of the TENS and the vibration source and transfer the force of vibration to the skin. These electrodes need to be flexible to adapt to the contours of the skin 2, especially if the electrodes need to adhere to the skin 2. However, flexible materials do not transfer the forces of vibration efficiently. Also, the only vibration direction that can be transferred effectively in Vallero's device is a back-and-forth motion vibration, parallel to the skin 2 which would not result in an effective deeper soft-tissue anesthesia, as opposed to a motion perpendicular to the skin 2 which is a more effective way of producing an anesthesia in deeper tissues. Therefore a larger, heavier, and bulkier vibrating system would be required to increase the forces generated by vibrations in his device. And 2) vibrating the skin and the underlying tissues during the insertion of a needle is contraindicated as it would exacerbate the pain of skin and tissue puncture as vibration would repeatedly bring the tissues in contact with the cutting edge of the needle or another sharp object that is penetrating the tissue. It would be more comfortable for the recipient if the vibration would stop before the needle is inserted into the recipient. Therefore, in a different example of the Invention, a vibrating device 17 is positioned on a plurality of electrodes 1 and presses them against the skin 2 and provides vibration to the recipient's skin 2 in a motion generally perpendicular to the surface of the skin 2, FIG. 7. The electrodes 1 apply TENS pulses to the skin 2 before, during, and/or after vibration to the skin 2. After the vibration stops, the skin 2 and the underlying tissues are painlessly punctured. The anesthetic effects of the combination of vibration and TENS last even after the cessation of vibration and TENS for several seconds up to many minutes. This is especially true if the application of TENS is extended close to or up to the time of injection. In an example of the invention, the vibrating device 17 includes one or more electrodes 1 and presses them against the skin 2 as in FIG. 7. For example, the electrodes may transfer the vibration to the skin 2. In an example of the invention, the vibrating device 17 is included in the syringe 6 that can be held firmly against the skin 2 to effectively transfer the vibrating forces to the vicinity of the skin 2 puncture site, FIG. 8.

In order to further reduce the size of Vallero's vibrating system and still maintain strong enough vibrating forces, the following design is proposed. At least one of the electrodes 1 that transfer the vibration to the recipient's skin is structured so as to amplify the vibration peak-to peak amplitude. This can be done in various ways. For example, use can be made of springs running through said at least one electrode 1 that would vibrate and amplify the amplitude of the vibration they receive from the vibration system at a specific vibration frequency emitted by the vibration system. Therefore, if the vibration frequency of the vibration system is known in advance, the electrode 1 can be designed to amplify the vibration amplitude at that frequency. Therefore, a smaller, more compact vibration system can be used to emit strong enough vibration to generate anesthesia in conjunction with application of electricity.

Disclosed herein is also a kit for painless skin puncture. The kit includes an electric current generator such as a TENS device 9, one or more electrodes 1, one or more barriers 21, and one or more skin puncture means 5 such as a syringe 6 or a lancing device 13. At least ore electrode 1 may be included in the skin puncture means 5 or in at least one barrier 21.

A method of painless or near painless skin puncture, such as an injection, is disclosed including applying electricity through a plurality of electrodes 1 to the vicinity of the puncture site for a required period of time at least before, during, or after puncturing the skin 2 and tapping the tissue at or in the vicinity of the puncture site at least before, during, or after the puncturing of the skin. In this method, the force of tapping required is less than slapping. In another example of the invention, at least either the tapping or the application of electricity to the vicinity of the puncture site is terminated at least one second before puncturing the skin. Since the steps in these methods may be performed sequentially, these methods can be performed requiring only one hand. Furthermore, they may be performed slowly and carefully. One or more electrodes 1 may be included in a skin puncture means 5. Also one or more electrodes 1 may perform the tapping for convenience. Furthermore, the tapping may be performed directly onto the skin 2 or on one or more barriers 21, placed at or in the vicinity of a puncture site, which in turn transfer the impact of the tapping to the underlying skin 2. One or more electrodes 1 may be included in one or more barriers 21.

Also a method of near painlessly or painlessly puncturing the skin of a recipient is disclosed including rubbing the puncture site or its vicinity once or more before, during, or after puncturing the skin 2 and application of electricity to the puncture site or its vicinity before, during, or after puncturing the skin 2. The rubbing may be performed by at least one electrode that supplies electricity to the puncture site or its vicinity. The means that performs the rubbing may also rub dry some disinfectant placed on said skin. Furthermore, a method of near painlessly or painlessly puncturing the skin of a recipient is disclosed including applying pressure to the puncture site or its vicinity for a required duration once or more before, during, or after puncturing said skin and application of electricity to the puncture site or its vicinity for a required duration before, during, or after puncturing said skin. The pressure may be applied using one or more electrodes 1 in order to mimic a human touch.

In addition, a method of painlessly or near painlessly puncturing the skin is disclosed in which an antiseptic with a relatively low boiling point is applied to the puncture site and its vicinity to which a flow of gas is applied so as to blow and dry said antiseptic away at least before, during, or after an application of electricity to the puncture site or its vicinity at least before, during, or after a skin puncture.

Also a method of painless or near painless skin puncture is disclosed including applying electricity at least before, during, or after applying physical stimulation, each for a required duration, said physical stimulation being in the form of at least tapping, rubbing, applying pressure, or vibration, to the vicinity of the skin puncture site, then stop at least said electrical application or said physical stimulation at least one or more seconds before the skin puncture. This method may require the use of only one hand. One may for example, perform first tapping the skin puncture site either by fingers or a skin puncture means 5 that includes one or more electrodes 1 that can come in contact with the recipient's skin 2, then holding the skin puncture means 5 so as to apply electricity such as TENS through said one or more electrodes 1 to the vicinity of the puncture site, and then puncturing the skin 2. In one example of the Invention, applying electricity to the vicinity of the skin puncture site is stopped at least one or more seconds before the skin puncture. Also one may stop applying the physical stimulation to the skin puncture site or its vicinity at least one or more seconds before the skin puncture.

The methods of obtaining anesthesia on the recipient's skin 2 described in this patent application are applicable to the mucosa, for example attached and loose gingiva in the oral cavity. Furthermore, these methods are also applicable to other mammals than human beings.

Even though the reference above is made regarding injections, it is clear to one skilled in the art that the anesthetic effects are applicable to various skin punctures and other usually painful skin procedures such as epilation and electrolysis.

One skilled in the art will appreciate that the present invention can be practiced by other than the described embodiments, which are presented here for purposes of illustration and not of limitation, and the present invention is limited only by the claims that follow.

What I claim is:

1. A method to reduce pain of an injection by a needle comprising:
   a) applying electric current through a plurality of electrodes at least before, during, or after the injection to an injection site of a patient, and
   b) applying gas to said injection site through a nozzle at least before, during, or after the injection to said injection site; and
   wherein pressing at least one of said electrodes on a skin of the patient causes said applying of gas.

2. The method according to claim 1 wherein said gas dries or blows away a disinfectant that has been applied to said injection site.

3. The method according to claim 2 wherein said gas is air.

4. The method according to claim 3 wherein said disinfectant has a boiling point selected to impart a cold sensation when said air blows on said disinfectant.

5. The method according to claim 1 further comprising pressing at least one of said electrodes on the skin to cause said applying electric current.

6. The method according to claim 1 wherein said gas is applied in discrete bursts.

7. The method according to claim 6 wherein
   a) said bursts of gas are of variable sequence, duration, and strength,
   b) said electric current is a plurality of electric pulses that are of variable sequence, duration, and strength, and
   c) at least one of the sequence, duration, and strength of said bursts of gas and at least one of the sequence, duration, and strength of saki electric current application are coordinated such that at least one of the electric pulses and at least one of the bursts of compressed gas occur simultaneously.

8. The method according to claim 6 wherein
   a) said bursts of gas have at least one of a sequence, a duration, and a strength,
   b) said electric current has a plurality of electric pulses that have at least one of a sequence, a duration, and a strength, and
   c) at least one of the sequence, duration and strength of said bursts of gas and at least one of the sequence, duration, and strength of said electric pulses are coordinated such that at least one of the electric pulses and at least one of the bursts of gas occur simultaneously.

9. The method according to claim 1 wherein said electric current is TENS.

10. The method of claim 1 wherein said nozzle is disposed between at least two of said plurality of electrodes.

11. The method according to claim 1 wherein a can containing compressed gas applies said gas, and wherein said can includes said plurality of electrodes, and wherein said applying of electric current is actuated by pressing at least one of said plurality of electrodes to the skin.

12. The method according to claim 11 wherein said applying of gas includes applying a plurality of discrete bursts of compressed gas.

13. A method to reduce pain of an injection by a needle comprising:
   a) applying electric current through a plurality of electrodes at least before, during, or after the injection to an injection site, and
   b) applying gas to said injection site through a nozzle at least before, during, or after the injection to said injection site,
   wherein said plurality of electrodes are included in a retaining means and positioned so as to come in contact with a recipient's skin and apply electric current to the vicinity of said injection site at least before, during, or after the injection,
   wherein said nozzle is included in said retaining means and positioned so as to apply gas to the injection site at least before, during, or after the injection; and
   wherein pressing at least one of said electrodes on the skin of the recipient causes said applying of gas.

14. The method according to claim 13 wherein said gas is applied to the injection site before and during the injection.

15. The method according to claim 14 wherein said applying of electricity is actuated by pressing at least one of said plurality of electrodes to the skin.

16. The method according to claim 13 wherein
   a) said nozzle applies a plurality of discrete bursts of compressed gas.

17. The method according to claim 13 wherein
   a) said nozzle applies a plurality of discrete bursts of compressed gas, the discrete bursts having at least one of a sequence, a duration, and a strength, and
   b) at least two or more of said electrodes apply an electric currently having a plurality of electric pulses that have at least one of a sequence, a duration, and a strength,
   at least one of the sequence, duration and strength of said bursts of compressed gas and at least one of the sequence, duration, and strength of said electric current application are coordinated such that at least one of the electric pulses and at least one of the bursts of compressed gas occur simultaneously.

18. A method to reduce pain of a needle insertion into a recipient's skin comprising:
   a) applying electric current through a plurality of electrodes at least before, during, or after the insertion of said needle to an insertion site,
   b) blowing gas to saki insertion site before and during the insertion of said needle into saki insertion site; and
   wherein pressing at least one of said electrodes on the skin of the recipient causes said applying of gas.

19. The method according to claim 18 wherein said applying of electric current is actuated by pressing at least one of said plurality of electrodes to the skin.

* * * * *